United States Patent [19]
Oki et al.

[11] 4,370,213
[45] Jan. 25, 1983

[54] OXYGEN SENSOR
[75] Inventors: Shuichiro Oki, Aichi; Tetsuo Watanabe, Nagoya, both of Japan
[73] Assignee: NGK Insulators, Ltd., Nagoya, Japan
[21] Appl. No.: 264,240
[22] Filed: May 18, 1981
[30] Foreign Application Priority Data May 29, 1980 [JP] Japan .................. 55/73112[U]

[51] Int. Cl.³ .................................................. G01N 27/46
[52] U.S. Cl. ................................. 204/195 S; 174/65 R
[58] Field of Search ........................ 204/1 S, 195 S; 174/65 R

[56] References Cited
U.S. PATENT DOCUMENTS

| 4,123,131 | 10/1978 | Pearce et al. | 204/195 S |
| 4,145,272 | 3/1979 | Nakamura et al. | 204/195 S |
| 4,175,019 | 11/1979 | Murphy | 204/195 S |
| 4,212,720 | 7/1980 | Maurer et al. | 204/195 S |

FOREIGN PATENT DOCUMENTS 55-373  3/1980  Japan ......................... 204/195 S Primary Examiner—T. Tung
Attorney, Agent, or Firm—Stevens, Davis, Miller & Mosher

[57] ABSTRACT

An oxygen sensor having a high reliability without penetration of water is disclosed. The oxygen sensor has a solid electrolyte consisting of a tubular body closed at its one end, having inner and outer electrodes, and received gastightly in a housing; a center conductor pressed and electrically connected to the inner surface electrode by a pressing force of a spring; an outwardly extended rim formed at the end portion of a tubular connecting terminal, which penetrates through a first insulating body supported by the upper end of a metallic container connected to the housing and is connected to the center conductor through a conductor; and a second insulating body which is slidable with respect to the metallic container and is arranged between another end of the above described spring, which is connected at its one end to the center conductor having the same potential as that of the inner electrode, and the rim of the connecting terminal.

3 Claims, 4 Drawing Figures

FIG.1
PRIOR ART
FIG.2
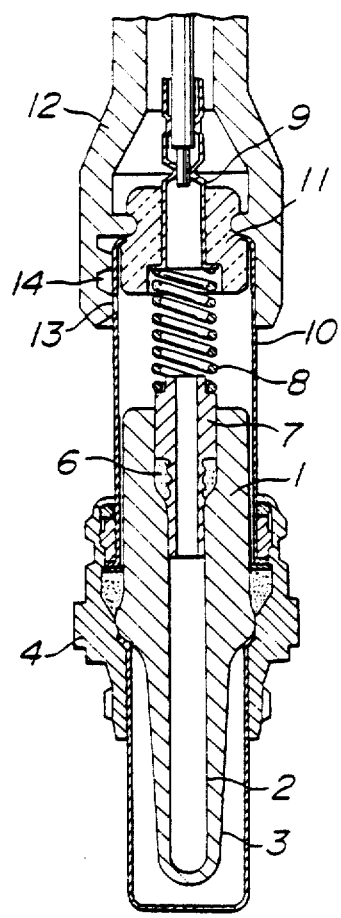
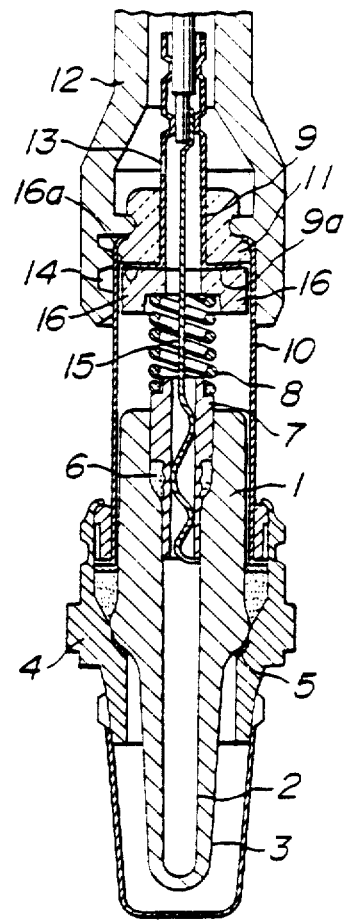

OXYGEN SENSOR

BACKGROUND OF THE INVENTION (1) Field of the Invention

The present invention relates to an oxygen sensor used for measuring the oxygen concentration in the exhaust gas of internal combustion engines by using an oxygen concentration cell consisting essentially of a solid electrolyte.

(2) Description of the Prior Art

There has hitherto been widely known an oxygen sensor which is used for measuring the oxygen concentration in the exhaust gas of internal combustion engines, such as in automobiles and the like, by using an oxygen concentration cell consisting essentially of a solid electrolyte, such as zirconia or the like, and for controlling the air/fuel ratio with a high accuracy. In a conventional oxygen sensor shown in FIG. 1, a tubular solid electrolyte 1 closed at its one end and having inner and outer electrodes 2 and 3 formed on its inner and outer surfaces, respectively, is gastightly received in a housing 4. The outer electrode 3 is electrically connected to the housing 4, and the inner electrode 2 is electrically connected to a center conductor 7 through a flexible conductive material 6. The center conductor 7 is pressed towards the solid electrolyte 1 by means of a spring 8 to secure its electric contact with the inner electrode 2 and to conduct the potential of the inner electrode 2 to a connecting terminal 9 through the spring 8. Further, the connecting terminal 9 is fitted in and covered with an insulating body 11 in order to insulate electrically the connecting terminal 9 from a metallic container 10 contacted with the housing 4 having the same potential as that of the outer electrode 3. However, in the oxygen sensor having the above described structure, when an external force (often caused on handling the said oxygen sensor) is applied to the connecting terminal 9 in a direction perpendicular to the axis of the oxygen sensor, the insulating body 11 is inclined due to the presence of a space between the insulating body 11 and the metallic container 10, and a lateral force acts upon the spring 8 fitted into the concave portion of the insulating body 11, and hence contact failure occurs in the fitted portion of the center conductor 7 in the solid electrolyte to cause unstable electrical connection between the inner electrode 2 and the center conductor 7, and to cause cracks in the solid electrolyte 1 due to the stress caused by the irregular pressure applied thereto by the center conductor 7.

Furthermore, in the oxygen sensor having the above described structure, an air inlet opening 13 is formed in the metallic container 10 and the distance from the tip of a boot 12 to the said air inlet opening 13 is very short, and therefore when an automobile is splashed with water while running, water penetrates easily into the interior of the metallic container 10, and the solid electrolyte 1 is rapidly cooled and is broken. The inventors have succeeded in overcoming the above described drawbacks of conventional oxygen sensors.

SUMMARY OF THE INVENTION

The object of the present invention is to provide an oxygen sensor which is free from the unstable electric connection between an inner electrode and a center conductor caused by application of an external force in a direction perpendicular to the axis of the oxygen sensor, is free from irregular pressure applied to the solid electrolyte, and allows very little penetration of water upon splashing with water.

That is, the feature of the present invention is the provision of an oxygen sensor wherein a solid electrolyte consisting of a tubular body closed at its one end and having inner and outer electrodes formed on its inner and outer surfaces respectively is gastightly received in a housing, and a center conductor is pressed and electrically connected to the inner electrode by a pressing force of a spring, the improvement comprising an outwardly extending rim formed at the end portion of a tubular connecting terminal, which penetrates through a first insulating body supported by the upper end of a metallic container connected to the housing and is connected to the center conductor through a conductor; and a second insulating body slidable with respect to the metallic container and arranged between another end of the above described spring, which is connected at its one end to the center conductor having the same potential as that of the inner electrode, and the rim of the connecting terminal.

BRIEF DESCRIPTION OF DRAWINGS

FIG. 1 is a cross-sectional view of one embodiment of a conventional oxygen sensor explained above;

FIG. 2 is a cross-sectional view of one embodiment of the oxygen sensor of the present invention.

DESCRIPTION OF THE PREFERRED EMBODIMENT

Figure 3:
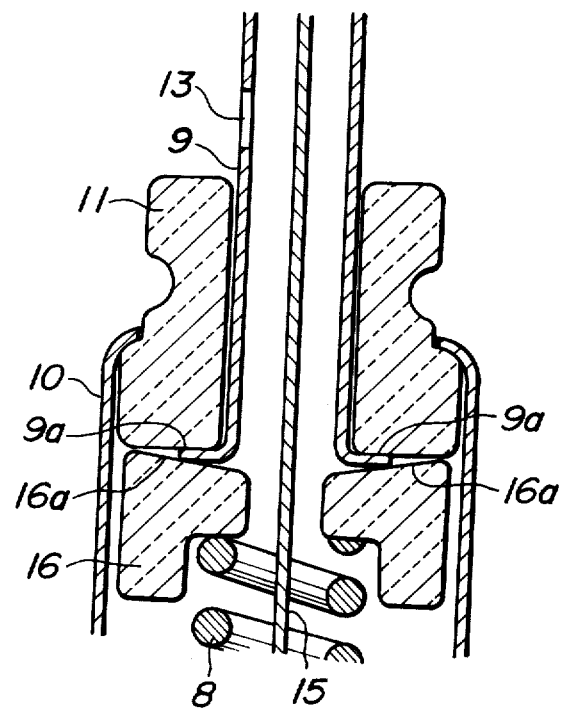
FIGS. 3 and 4 are cross-sectional views, in an enlarged scale, of a second insulating body and its neighbourhood in another embodiment of the oxygen sensor according to the present invention.

FIG. 2 illustrates one embodiment of the oxygen sensor according to the present invention. In the oxygen sensor, a tubular solid electrolyte 1 consisting of zirconia ceramic material, closed at its one end, and provided on its inner and outer surfaces with porous inner and outer electrodes 2 and 3 respectively, each consisting of a conductive material, such as platinum or the like, is gastightly received in a housing 4. The outer electrode 3 is electrically contacted with the housing 4 through a conductive packing 5 and the inner electrode 2 is electrically contacted with a center conductor 7 through a flexible conductive material 6, such as graphite or the like. The center conductor 7 is pressed to the solid electrolyte 1 by one end of a spring 8 to keep more completely the electrical connection between the center conductor 7 and the inner electrode 2. A first insulating body 11 is arranged between a connecting terminal 9, which is electrically connected to the center conductor 7 through a conductor 15, and a metallic container 10, which is connected to the housing 4 connected electrically to the outer electrode 3, in order to insulate electrically the connecting terminal 9 from the metallic container 10. One end of the tubular connecting terminal 9 extending through the first insulating body 11 is outwardly extended to form a rim 9a, and a second insulating body 16 is arranged between the rim 9a of the connecting terminal 9 and another end of the above described spring 8, one end of which is connected to the center conductor 7. The second insulating body 16 is formed such that the body is freely slidable with respect to the metallic container 10 arranged on the outer periphery of the second insulating body 16. Further, it is preferable that the second insulating body 16 is formed into an inclined surface at a contact surface 16a, which contacts with the rim 9a of the connecting terminal 9.

Figure 4:
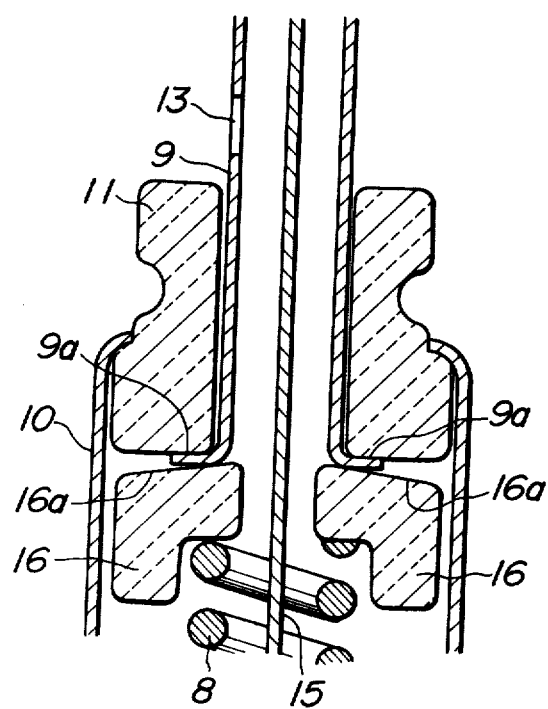

The inclined surface 16a of the second insulating body 16 may be an inclined surface having a falling gradient towards the center of the body 16 as illustrated in FIG. 3, or may be an inclined surface having a falling gradient towards the periphery of the body 16 as illustrated in FIG. 4. Furthermore, the inner diameter of the second insulating body 16 is preferred to be smaller than the inner diameter of the tubular connecting terminal 9 in order to prevent the penetration of water into the interior of the solid electrolyte when the oxygen sensor is splashed with water. An air inlet opening 13 is formed in the connecting terminal 9 at the neighborhood of a crimping-connecting portion 17 of the connecting terminal 9 and the conductor 15, and the outer peripheral portion of the first insulating body 11 is fitted in and covered with a boot 12.

The oxygen sensor of the present invention has the above described structure. Therefore, even when an external force is applied to the connecting terminal 9 in a direction perpendicular to the axis of the oxygen sensor, the rim 9a of the connecting terminal 9 slides on the contacting surface of the second insulating body 16, and the second insulating body 16 slides and moves in the axial direction of the metallic container 10, and hence the spring 8 stretches only in its axial direction. Accordingly, contact failure does not occur at the fitted portion of the center conductor 7 in the solid electrolyte 1, and moreover since the spring 8 does not cause irregular pressure, breakage of the solid electrolyte 1 due to the stress applied thereto through the inner surface does not occur.

In the oxygen sensor of the present invention, air used as a reference atmosphere is flowed into or flowed out from the interior of the solid electrolyte 1 through the air inlet opening 13 formed in the sidewall of the connecting terminal 9 in the vicinity of the portion connected to a lead wire, and therefore the distance of the air inlet opening 13 from the boot end is very long, and even when the oxygen sensor is splashed with water, the water hardly penetrates into the interior of the oxygen sensor. Even when water penetrates into the interior of the connecting terminal, the water is interrupted by the second insulating body 16 and hardly reaches the interior of the solid electrolyte 1, and breakage of the solid electrolyte due to splashing of water is very rare.

As described above, the oxygen sensor of the present invention has the following merits; since a second insulating body is arranged between the rim of a connecting terminal and a spring, irregular pressure and stress due to the displacement of the connecting terminal do not transmit directly to the center conductor, and therefore the center conductor is free from failure in its contact with the inner electrode; since the center conductor is connected to the connecting terminal through a conductor, the connection has a high reliability; even when the oxygen sensor is splashed with water, the solid electrolyte does not break; and the like. Therefore, the oxygen sensor can be used for measurement and detection of oxygen concentration in exhaust gas of various automobiles, and is very useful for the purpose of energy saving and prevention of public nuisance.

What is claimed is:

1. In an oxygen sensor, wherein a solid electrolyte consisting of a tubular body closed at its one end and having inner and outer electrodes formed on its inner and outer surfaces respectively is gastightly received in a housing, a center conductor is pressed against the inner electrode by a pressing force of a spring connected to said center conductor, a tubular connecting terminal is electrically connected to said center conductor by a second conductor, and a metallic container receives a portion of an open end of said tubular body and said center conductor, the improvement comprising:
a first insulating body supported by the upper end of said metallic container;
said tubular connecting terminal having an outwardly extending rim formed at an end portion thereof and penetrating through said first insulating body;
said spring being slidable with respect to said metallic container; and
a second insulating body being arranged between said rim and said spring and being axially slidable.

2. An oxygen sensor according to claim 1, wherein the second insulating body is formed into an inclined surface at the surface which contacts with the rim of the connecting terminal.

3. An oxygen sensor according to claim 1 or 2, wherein an air inlet opening is formed in the connecting terminal at the neighborhood of a crimping-connecting portion of the connecting terminal and the conductor.

* * * * *